United States Patent [19]

Jensen

[11] Patent Number: 4,538,617

[45] Date of Patent: Sep. 3, 1985

[54] TRANSDUCER FOR THE SIMULTANEOUS MEASUREMENT OF DIFFERENT PHYSIOLOGICAL QUANTITIES

[76] Inventor: Arne Jensen, Am Hannes 4, D-6301 Grossen-Linden - Leihgestern, Fed. Rep. of Germany

[21] Appl. No.: 434,105

[22] Filed: Oct. 13, 1982

[30] Foreign Application Priority Data

Oct. 13, 1981 [DE] Fed. Rep. of Germany ....... 3140673

[51] Int. Cl.$^3$ ............................. A61B 5/00; A61B 5/04
[52] U.S. Cl. ..................................... 128/635; 128/640; 128/641
[58] Field of Search .......................... 128/635, 639–643

[56] References Cited

U.S. PATENT DOCUMENTS

| 3,750,650 | 8/1973 | Ruttgers | 128/642 |
| 4,209,020 | 6/1980 | Nielsen | 128/640 |
| 4,294,258 | 10/1981 | Bernard | 128/635 |
| 4,308,873 | 1/1982 | Maynard | 128/642 X |

FOREIGN PATENT DOCUMENTS 2930663 2/1981 Fed. Rep. of Germany ...... 128/635

Primary Examiner—Lee S. Cohen
Attorney, Agent, or Firm—Fleit, Jacobson, Cohn & Price

[57] ABSTRACT

In the case of a transducer for the simultaneous measurement of different physiological quantities, with a measuring head which contains a transducer for measuring a first physiological quantity and a transducer having electrodes connectable with signal processing electronics for measuring a bioelectric quantity as a further physiological quantity, and comprises a contact surface by means of which it can be contacted with the human or animal body, it is provided for obtaining a reliable measurement of the heart potentials, particularly of a foetus at the time of birth, that one of the electrodes is arranged in such a way that, together with the contact surface, it comes into contact with the human or animal body, while a further electrode is located outside the contact surface of the measuring head.

5 Claims, 3 Drawing Figures

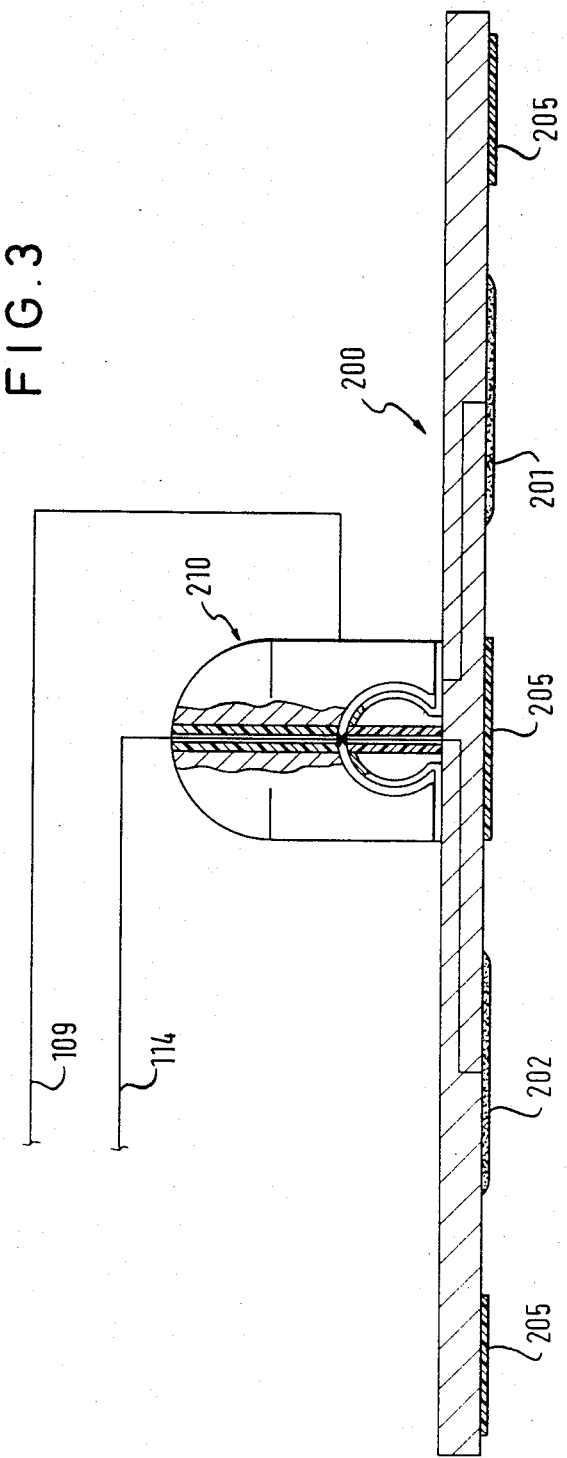

TRANSDUCER FOR THE SIMULTANEOUS MEASUREMENT OF DIFFERENT PHYSIOLOGICAL QUANTITIES

BACKGROUND OF THE INVENTION

The invention relates to a transducer for the simultaneous measurement of different physiological quantities, with a measuring head containing a transducer for measuring a first physiological quantity and a transducer having electrodes connectable to signal processing electronics for measuring a bioelectrical quantity as a further physiological quantity, and comprising a contact surface by means of which it can be engaged with the human or animal body, at least a first one of said electrodes being located at the measuring head to contact with the human or animal body together with the contact surface.

Transducers containing measuring members for the simultaneous measurement of different physiological quantities are always important in medicine, if the application of a large number of measuring members is difficult for time or space reasons, or because it stresses the patient. A typical example is the problem of fitting measuring members to the head or buttocks of a foetus still in the uterus at the time of birth. In the case of a known transducer of the aforementioned type (DOS No. 2,930,663) a transducer for the polarographic measurement of the oxygen partial pressure and a transducer for measuring heart potentials (electrocardiogram) are combined with one another in a measuring head. The ECG electrodes in this known transducer are all located in the contact surface through which the measuring head is applied. In view of the necessarily small size of the measuring head and consequently its contact surface, it is a disadvantage of this electrode arrangement that due to their resulting close spatial proximity, there is a considerable risk of a short-circuit between the electrodes. In addition, the potential differences to be measured are small and are therefore difficult to separate from interfering potentials.

BRIEF SUMMARY OF THE INVENTION

The problem of the invention is to so develop a measuring head of the aforementioned type that, particularly in connection with use during birth, the heart potentials can be reliably measured.

According to the invention, this problem is solved in that at least a second one of said electrodes is attached to the measuring head outside the contact surface thereof. Thus, in this arrangement, where one of the electrodes for measuring the heart potentials is located in the application surface and another one is located outside the same, particularly on the side of the measuring head remote therefrom, a short-circuit is substantially impossible, particularly if, as is standard practice, and necessary when measuring the oxygen partial pressure, the peripheral portion of the contact surface of the measuring head is adhered to the human or animal body by means of an adhesive, so as to seal the inner portion of the contact surface, it being ensured that the adhesive also passes round the electrode positioned in the contact surface. Amniotic fluid moisture or electrolytic cream ensures the necessary conductive connection between the electrode not located in the application surface and the human or animal body, on which the measurement is taking place. The amniotic fluid moisture or electrolytic cream is kept away from the electrode located in the contact surface by the adhesive. Even on taking account of the fact that the amniotic fluid moisture or electrolytic cream means that the electrode located outside the contact surface is brought electrically nearer to the electrode located in the contact surface, the distance between them is still greater than that if they were juxtaposed in the contact surface.

According to an advantageous further development of the invention, a bipolar plug and socket connection is provided on the measuring head, whose one pole is connected to the signal processing electronics by connection to the second one of said electrodes and whose other pole is also connected to the signal processing electronics. In this way, the measuring head can be connected via the plug connection with adhesive electrodes, which are directly applicable to the body, if the aforementioned amniotic fluid moisture is not available or if it is not possible to use electrolytic cream, in order e.g. to perform impedance measurements for recording the respiratory rate.

According to another advantageous development of the invention, the transducer is provided with an adhesive electrode body, having two insulated juxtaposed electrodes which can be brought into contact with the human or animal body and a further bipolar plug and socket connection, one pole of the latter being connected to one electrode and the second pole to the other electrode. Appropriately, there is a cable for connecting the measuring head to the adhesive electrode body which has plug connections complementary to the first plug connection and the further plug connection. Such a transducer only needs two measuring members, namely the measuring head and the adhesive electrode body, whereas previously four measuring members, namely a measuring head for measuring the oxygen partial pressure and three electrodes for measuring the heart potentials were required.

According to another advantageous development of the invention, the bipolar plug connection and the further bipolar plug connection are in each case formed by a pushbutton plug connection, the pushbutton body forming the one pole and an axial core insulated from the pushbutton body forming the second pole. This provides a particularly simple connection possibility between the measuring head and adhesive electrode body.

BRIEF DESCRIPTION OF THE DRAWINGS

The invention is described in greater detail hereinafter relative to non-limitative embodiments and with reference to the attached drawings, wherein show:

FIG. 3 a side view of an adhesive electrode body with a pushbutton plug.

DETAILED DESCRIPTION OF THE PREFERRED EMBODIMENTS

Figure 1:
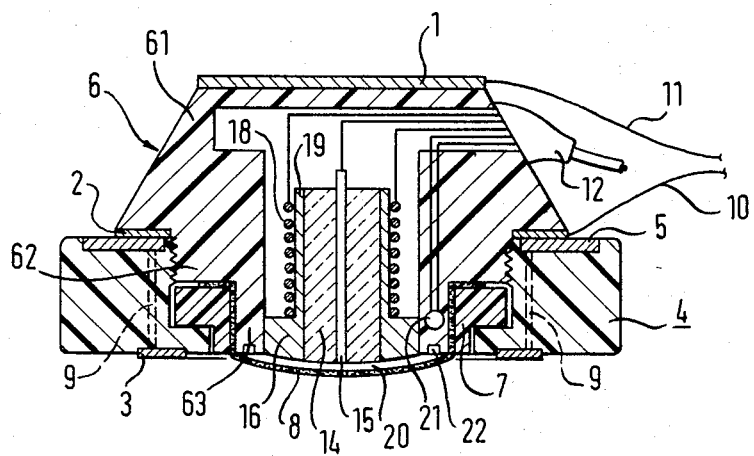
FIG. 1 an axial section through a measuring head according to the first embodiment.

FIG. 1 shows a measuring head for the simultaneous measurement of the transcutaneous oxygen partial pressure and the heart potential (electrocardiogram-ECG) with the foetus still in the uterus at the time of birth. The measurement of the transcutaneous oxygen partial pressure takes place polarographically with the represented measuring head.

The measuring head has a measuring head body 6 made from plastic, which geometrically has a substantially axially symmetrically stepped construction with an upper frustum-shaped portion 61, a lower threaded cylindrical portion 62 and below the latter a smaller diameter, cylindrical portion 63. The latter is surrounded by a stepped ring 7, which is also made from plastic, and whose internal diameter substantially corresponds to the diameter of the smaller diameter cylindrical portion 63 and which at the back engages with the larger diameter cylindrical portion 62. In the gap between cylindrical portion 62, 63 on the one hand and ring 7 on the other is secured an oxygen-permeable diaphragm 8, e.g. made from polytetrafluoroethylene (PTFE), which extends in front of the face of cylindrical portion 63 and, on fitting the measuring head e.g. to the head of the foetus, comes into contact with the latter. Behind diaphragm 8 is axially provided a reducing electrode 15 comprising a frontally free wire, preferably of platinum, sealed into a cylindrical glass member 14. Oxygen molecules diffused through diaphragm 8 are reduced on said electrode and the measured reducing current is a measure of the oxygen partial pressure in the tissue (e.g. the skin) to which the measuring head with its diaphragm 8 is applied. The reducing electrode is coaxially surrounded by an annular reference electrode 16, preferably made from silver. The reference electrode is heated by a filament winding 18, placed round a hollow cylindrical extension 19 of reference electrode 16 and which ensures that under the measuring electrode the skin is kept at a constant, elevated temperature, in order to ensure optimum blood supply (perfusion) and consequently the correct measurement of the oxygen partial pressure. The temperature is measured by means of a thermometer probe 21, e.g. formed by a thermistor. Between diaphragm 8 and the face of reducing electrode 15, glass member 14 and reference electrode 16 is located the electrolyte 20 necessary for the polarographic measurement and which is received also in an annular slot 22 in the face of portion 63. Glass member 14, in which is sealed the reducing electrode 15, and reference electrode 16, have a slightly crowned construction, in order to give the diaphragm 8 a slightly convex configuration at its contact face with the skin.

Onto the thread of cylindrical portion 62 is screwed a plastic nut 4, whose internal diameter is stepped in such a way that on screwing, the stepped ring 7 is pressed against cylindrical portion 62 and as a result diaphragm 8 is secured. The diaphragm-side face of nut 4 is essentially located in one place with diaphragm 8 and embedded therein is a metal ring, which projects somewhat out of the plane and together with diaphragm 8 gets in engagement with the skin. Metal ring 3 forms one of two electrodes for measuring the heart potential, the other electrode in the form of metal plate 1 being located outside the application surface on the rear side of the measuring head, i.e. that remote from the diaphragm. This remote side is the small face of the frustum-shaped portion 61. Metal ring 3 is connected by bolts or pins 9 passing in axial direction through plastic nut 4 with a further metal ring 5, which is embedded in or mounted on the side of nut 4 remote from the contact side. When nut 4 is screwed down, metal ring 5 engages with a further metal ring 2 fitted to the radial shoulder face between the frustum-shaped portion 61 and cylindrical portion 62. One (10) of two leads 10, 11 is connected to metal ring 2, said leads leading to an electrocardiograph. The other lead 11 is connected to plate 1. As a result of this construction, nut 4 can be removed, despite the electrical connected between metal ring 3 and lead 10 in the screwed-down state, and without hanging on a particular lead, i.e. both leads pass to the measuring head body 6. Cable 12 for measuring the oxygen partial pressure also passes away from body 6.

When measured externally on nut 4, the diameter of the measuring head is approximately 20 mm, whilst its height and therefore the spacing of the electrodes formed by metal plate 1 and metal ring 3 is approximately 10 mm.

For measurement purposes, the measuring head is, for example, stuck to the head or buttocks of the baby. The metal ring 3 embedded in nut 4 comes into contact with the skin, together with the diaphragm. Adhesion takes place by means of an adhesive paste applied in such a way that the latter also surrounds metal ring 3 and consequently prevents any access of amniotic fluid moisture thereto. As has already been stated, the metal ring 2 located on the measuring head body 6 is in conductive connection via metal ring 5 and bolts or pins 9 with the metal ring 3 on the foetal side embedded in the adhesive surface. Since the natural wetness of the foetus at the time of birth provides a conductive connection from the foetal body to electrode 1, but not to metal ring 3 as a result of the adhesive and, whilst taking account of the amniotic fluid, there is also an adequate spacing between the effective electrodes, this arrangement makes it possible to record the foetal electrocardiogram and by means of a R-peak analysis a beat-by-beat heart rate recording is made possible. In addition to this, the transcutaneous oxygen partial pressure $pO_2$ can be measured, together with a previously unmentioned skin blood supply measurement, which is based on the measurement of the electric current required for producing the elevated skin temperature by means of the silver heating electrode. The better the perfusion of the skin, the greater the heat removal through the blood, and consequently the necessary heating current.

The two electrocardiogram leads 10, 11 passing away from the measuring head are fixed in the plug of commercial cardiotocographs, whilst cable 12 which contains the connecting leads for electrodes 15, 16, filament winding 18 and thermometer probe 21 is connected to corresponding signal processing electronics.

As a result of the previously described arrangement, it is possible with a single measuring head to simultaneously record the heart rate, the skin perfusion and the transcutaneous oxygen partial pressure for diagnosing the foetal circulation shock syndrome. The fitting of the electrode formed by metal plate 1 to the side of the measuring head remote from the contact side ensures, without taking up additional space, a good spacing of the two effective electrocardiogram electrodes, which supplies easily measurable potential differences.

The measuring head was tested under birth conditions, whilst measuring the foetal heart rate (using HEWLETT PACKARD 8030 cardiotocograph), labour pains (directly by means of HEWLETT PACKARD 8030 cardiotocograph), the relative local skin perfusion (via HELLIGE oxymonitor) and the transcutaneous foetal $pO_2$ (via HELLIGE oxymonitor). All signals were satisfactorily recorded up to the actual time of birth.

Figure 2:
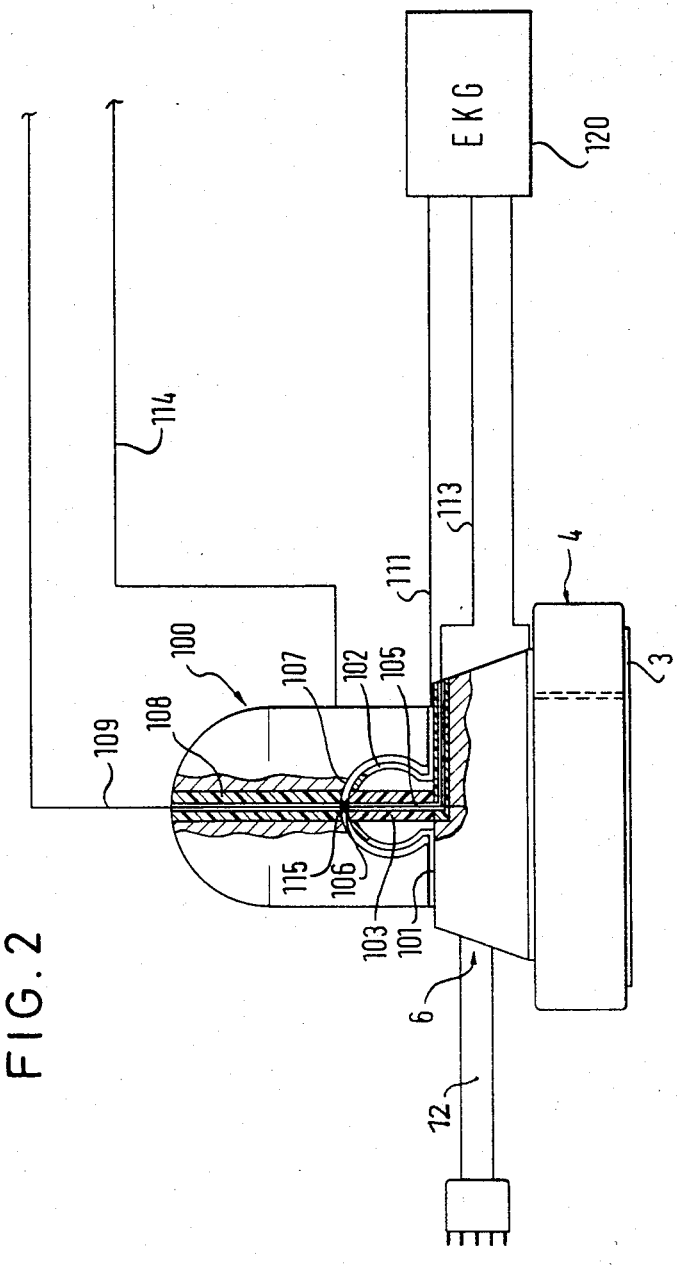
FIG. 2 a part sectional side view of a measuring head according to a second embodiment with diagrammatically represented connected means.

FIG. 2 shows a transducer, which in particular permits a measurement which is independent of existing wetness or electrolytic cream, and which is also suitable for an impedance measurement with a view to a measurement of the respiratory rate.

With regards to the measuring head body 6 and the cooperating nut 4, the measuring head is constructed in the same way as that of FIG. 1. The polarographic measurement device contained within the same is also provided in the same way as in FIG. 1.

However, the following constructional differences exist. Metal plate 1 of FIG. 1 is replaced by a metal plate 101 (the second electrode), containing in its centre the male part 102 or first pole of a pushbutton plug 100 as part of the bipolar plug. Part 102 has an axial bore, which is filled with plastic 103 and in which is guided a line 105 which is part of the second pole insulated by the plastic from the remaining contact body of part 102. Line 105, coupled to the second pole, also continues in the head part, where it is once again insulated by means of plastic from metal plate 101 and continues on as line 113 to an electrocardiograph 120. Plate 101 is connected via line 111 to the electrocardiograph. Line 105 passing through part 102 of the pushbutton plug ends at a contact point 106, located in the axis of part 102.

On the counterpart or complementary of pushbutton plug is provided the female part 107, which is in contact with male part 102 when the connection is closed. Female part 107 also contains an axial bore in which is guided a line 109, which is insulated from the remainder of part 107 by plastic 108 and via which is connected a first electrode 201 of an adhesive electrode body 200 shown in FIG. 3. A line 114 connected with a second electrode 202 of the adhesive electrode body is connected to the body of the female part 107.

In the same way as line 105 ends at a contact point 106, line 109 ends in the axis of female part 107 at a contact point 115. In the case of a joined connector, the contact points 106 and 115 are in contact with one another and consequently form the connection between lines 105 and 109.

The adhesive electrode body 200 shown in FIG. 3 is an elliptical or circular disk on which are provided a first juxtaposed electrode 201 and a second juxtaposed electrode 202 as circular disks, an adhesive foil 205 being provided on the body surrounding the electrodes. For connecting electrodes 201, 202 to lines 109, 114 there is a pushbutton plug connection 210 or further bipolar plug, one part of which is on the said lines and the other part of which is on the adhesive electrode body 200. Connection 210, including the axial bushings and the connection points, is constructed in exactly the same way as the pushbutton connection 100 on the measuring head side.

In this embodiment of the transducer, the heart potentials are obtained from the patient's body by means of electrodes 201 (via the pushbutton plug in plug 210, line 109, line 105 and line 113), 202 (via the internal axial line in plug 210, line 114, complementary pushbutton plugs 102 and 107 and line 111) and the electrode formed by metal ring 3.

This transducer embodiment permits a simultaneous measurement of a gas partial pressure and heart action currents with three electrodes and in all only two measuring members. For the same measurement, originally four measuring members were required, namely a measuring head for measuring the gas partial pressure and three individual electrodes for measuring the heart potentials.

Since in the case of a corresponding fitting, the electrode body and the measuring head can move relative to one another during the rise and fall of the thorax which, by means of an impedance measurement, makes it possible to measure the respiratory rate, this embodiment provides a further advantage compared with the first embodiment.

What is claimed is:

1. A device for the simultaneous measurement of at least two different physiological quantities of a human or animal body and being connectable to signal processing electronics, comprising:
   a measuring head containing a transducer for measuring a first physiological quantity and a contact surface means for engaging with said human or animal body;
   a first one of a pair of electrodes being located at the contact surface means to contact with said human or animal body together with said contact surface means and having means for electrically coupling to said signal processing electronics;
   a second one of said pair of electrodes being attached to the measuring head outside said contact surface means thereof and having connection means for electrically coupling to said signal processing electronics;
   a bipolar plug connection having first and second poles, said bipolar plug being removably fitted to said measuring head, said first pole being coupled to said second one of said pair of electrodes for coupling to said signal processing electronics by connection to said second one of said pair of electrodes and said second pole having means for electrically coupling to said signal processing electronics; and
   an adhesive electrode body having two insulated juxtaposed electrodes each of which are adapted for contact with said human or animal body, said adhesive electrode body including a further removable bipolar plug connection having third and fourth poles, said third pole being coupled to one of said juxtaposed electrodes and said first pole and said fourth pole being coupled to the other of one of said juxtaposed electrodes and said second pole.

2. A device according to claim 1, wherein said second one of said electrodes is arranged on the side of the measuring head remote from the contact surface means.

3. A device according to claim 1, wherein said bipolar plug connection is formed by a pushbutton plug connection, the pushbutton body thereof forming said first pole and an axial core thereof being insulated from said pushbutton body and forming said second pole.

4. A device according to claim 3, wherein said further bipolar plug connection is formed by a further pushbutton plug connection, the pushbutton body thereof forming said third pole and an axial core thereof being insulated from said pushbutton body and forming said fourth pole.

5. A device according to claim 4, wherein a cable having plug connections complementary to said pushbutton plug connection and said further pushbutton plug connection is provided as the means for electrically coupling the poles of the pushbutton plug connections.

* * * * *